United States Patent [19]
Greaves et al.

[11] Patent Number: 5,689,914
[45] Date of Patent: Nov. 25, 1997

[54] METHOD OF HYBRID CROP PRODUCTION USING DEHYDRATED POLLEN FROM STORAGE

[75] Inventors: John Andrew Greaves; Alan Francis Hawkins, both of Ankeny, Iowa; Raymond Russotti, Hudson, N.H.

[73] Assignee: Zenco (No. 4) Limited, London, England

[21] Appl. No.: 479,471

[22] Filed: Jun. 7, 1995

Related U.S. Application Data

[63] Continuation-in-part of Ser. No. 282,629, Jul. 29, 1994, Pat. No. 5,596,838, which is a continuation-in-part of Ser. No. 260,184, Jun. 15, 1994, abandoned.
[51] Int. Cl.$^6$ .............................. A01G 7/00; A01H 5/00; A01H 1/02
[52] U.S. Cl. .......................... 47/58; 47/1.41; 47/DIG. 1; 800/200; 426/419; 426/465
[58] Field of Search ....................... 47/58, 1.41, DIG. 1; 800/200; 426/419, 465

[56] References Cited

U.S. PATENT DOCUMENTS

| | | | |
|---|---|---|---|
| 4,746,071 | 5/1988 | Grünhoff et al. | 241/2 |
| 4,922,651 | 5/1990 | Atkinson et al. | 47/1.41 |

OTHER PUBLICATIONS

Barnabas, B. and E. Rajki. Fertility of deep frozen maize (Zea mays L.) pollen. Annals of Botany. 48:861–864, 1981.
Barnabas et al. Effect of pollen storage by drying and deep freezing on the expression of different agronomic traits in maize (Zea mays L.). Euphytica. 39:221–225, 1988.
Barnabas B; Fridvalszky L. "Adhesion and Germination of Differently Treated Maize Pollen Grains on the Stigma", pp. 329–332. Acta Bontanica Hungarica 30 (3–4) (1984), Abstract only.
Dereuddre, J; Blandin, S; Hassen, N. "Resistance of Alginate–Coated Somatic Embryos of Carrot (Daucus–Coarota L) to Desiccation and Freezing in Liquid–Nitrogen .1. Effects of Preculture", pp. 125–134. Cyro–Letters, vol. 12, (1991), Abstract only.
Dereuddre, J; Gazeau, C. "Natural Frost Resistance in Plants", pp. 7–25. Bulletin de la Societe Botanique de France, Actualites Bontaniques, 133 (3), (1986), Abstract only.
Dereuddre, J; Scottez, C; Arnaud, Y; Duron, M. "Resistance of Alginate–Coated Axillary Shoot Tips of Pear Tree (Pyrus Communis L. CV Beurre Hardy) in Vitro Plantlets to Dehydration and Subsequent Freezing in Liquid Nitrogen: Effects of Previous Cold Hardening—Shoot Tip Culture Encapsulation in Calcium Alginate Bead; Crypreservation and Plant Propagation; Germplasm Peservation", p. 31, 7, 317–23. C. P. Seances Acad. Sci, Serial 3, (1990), Abstract only.
Morisset, C; Gazeau, C; Hansz, J; Dereuddre., J. "Importance of Actin Cytoskeleton Behavior During Preservation of Carrot Cell–Suspensions in Liquied–Nitrogen", pp. 35–47. Protoplasm, vol. 173, (1993), Abstract only.

Nirde, P; Delbos, M; Combes, D. "New Procedure for Storing Pollen at Low Temperatures", pp. 211–212. Plant Physiology and Biochemistry, 26 (2), (1988), Abstract only.
Barnabas, B; Kovacs, G.; Abranyi, A.; and Pfahler, P. "Effects of Pollen Storage by Drying and Deep–Freezing on the Expression of Different Agronomic Traits in Maize (Zea mays L.)", Kluwer Academic Publishers, Dordrecht—Printed in the Netherlands, pp. 221–225.
Collins, T.C.; Lertmongkol, V.; and Jones, J.P. "Pollen Storage of Certain Agronomic Species in Liquid Air", Crop Science, vol. 13, Jul.–Aug. (1973), pp. 493–494.
Barnabas, B Preservation of Maize Pollen Biotechnology in Agriculture and Forestry, vol. 25 Maize (ed. by Y.P.S. Bajaj) Springer–Verlag Berlin Heidelberg (1994).
Barnabas, B. "Effect of Water Loss on Germination Ability of Maize (Zea mays L.) Pollen", Annals of Botany 55, pp. 201–204, (1985).
Barnabas, B. and Rajki, E. "Fertility of Deep–frozen Maize (Zea mays L.) Pollen" Agricultural Research Institute of the Hungarian Academy of Sciences, Annals of Botany Company (1981).
Barnabas, B. and Rajki, E. "Storage of Maize (Zea mays L.) Pollen at –196° C. in Liquid Nitrogen", Euphytica 25 (1976) pp. 747–752.
Nath, J. and Anderson, J.O. "Effect of Freezing and Freeze–Drying on the Viability and Storage of Lilium longiflorum L. and Zea mays L. Pollen", Cryobiology 12, pp. 81–88 (1975).
Daniel, L. "Retention of the Germinating Power of Pollen during Storage", Institute of Genetics of the Hungarian–Academy of Sciences, Budapest.
Connor, Kristina and Towill, Leigh. "Pollen–Handling Protocol and Hydration/Dehydration Characteristics of Pollen for Application to Long–Term Storage", Kluwer Academics Publisher (1993) pp. 77–84.
Walden, D.B. "Male Gametophyte of Zea mays L." Crop Science, vol. 7, Sep.–Oct. (1967) pp. 441–443.
Shands, H.L.; Janisch, D.C; and Dickson, A.D. "Germination Response of Barley Following Different Harvesting Conditions and Storage Treatments." Crop Science, vol. 7, Sep.–Oct. (1967).

Primary Examiner—David T. Fox
Assistant Examiner—Melissa L. Kimball
Attorney, Agent, or Firm—Dana Rewoldt

[57] ABSTRACT

The present invention relates to the development of a hybrid field production method which employs preserved pollen and a pollen bank for breeding purposes. Particularly, the present invention relates to a method of employing stored pollen in hybrid field production instead of employing pollen producing plants in the production field.

17 Claims, 6 Drawing Sheets

Fig. 6

METHOD OF HYBRID CROP PRODUCTION USING DEHYDRATED POLLEN FROM STORAGE

This application is a continuation-in-part of U.S. patent application Ser. No. 08/282,629 filed on Jul. 29, 1994, now U.S. Pat. No. 5,596,838, which is a continuation-in-part of U.S. patent application Ser. No. 08/260,184 filed on Jun. 15, 1994 which is now abandoned.

FIELD OF THE INVENTION

The present invention relates to the development of a hybrid field production method which employs preserved pollen and a pollen bank for breeding purposes. Particularly, the present invention relates to a method of employing stored pollen in hybrid field production instead of employing pollen producing plants in the production field.

BACKGROUND OF THE INVENTION

Plant breeding is one of the oldest recorded accomplishments of mankind. The ability to breed plants is an important mark in man's movement from nomadic life to organized society. Today's food crops are essentially the result of mankind's primitive plant breeding attempts.

The practice of plant breeding has progressed to a science. Plant breeding became a science when genetic principles gave predictability to plant breeding. Plant breeding is basically man's conscious selection of genetic material instead of nature's selection of genetic material. Examples of the successes of plant breeding are the increased productivity of field crops, development of insect resistant crops and disease resistant crops. The progression of the plant breeding science has been slowed by natural factors. These factors include: the length of time necessary for development of a plant to its sexual maturity, the length of time to pollen viability and the length of time to maturity of the pollen receptor. Presently plants, specifically maize, can only be pollinated when a plant is sexually mature, pollen is viable, and pollen receptors are available. Thus, if plants are cross pollinated such that the pollen of one plant is used to pollinate a second plant, the sexual maturity of both plants have to be coordinated to permit pollination to occur as the time period of pollen viability is limited in most crops. The method of increasing the efficiency and speed of plant breeding required the development of a system of storing pollen in a viable condition, a pollen bank. This eliminates the need to coordinate the timing of the sexual maturity of two plants and effectively eliminate one of the time factors in the plant breeding process. It eliminates plant breeding problems such as when pollen shed does not coincide with receptor maturity. Furthermore, the long term storage of viable pollen provides an unique ability to conserve and manipulate genetic resources. The ability to retrieve viable pollen, obtained from a group of individual plants stored for long periods of time provides great flexibility in plant breeding programs.

Methods for storage of viable pollen have been tested and some pollen can be stored. However, until the invention of the pollen dehydrating device, pollen from many row crops, especially maize, had not been successfully stored. Research on maize pollen storage had shown some limited success using air flotation when large quantities of pollen are stored. An air flotation method of drying prepared maize pollen for medium to long term storage. The system is somewhat limited as it does not allow the stored pollen to be readily used in a commercial breeding of hybrid field production program. The air flotation dries large quantities of pollen for storage. This stored pollen often has less than acceptable levels of viability when employed. This lack of viability made the use of stored pollen on a commercial basis somewhat unsatisfactory. Thus, only when the need for highly viable stored pollen was satisfied, could the remaining need to eliminate male plants in hybrid production fields also be satisfied. The present invention is a method of hybrid production without the male pollen producing plant.

SUMMARY OF THE INVENTION

The invention of the instrument and the germplasm bank (to produce large quantities of viable pollen) permitted the development of the present invention of a method of hybrid field crop production without the presence of both parent plants in small grain cereals the fields. Particularly in maize hybrid production fields.

An object of the present invention is to provide a unique method of hybrid field production employing viable stored pollen instead of male plants in the field.

A further object of this invention is to permit hybrid product of without reference to the nick between the flowering and pollen shed such that previously incompatible females and males can be crossed.

An object of the present invention is to provide a unique method of plant breeding employing viable stored pollen.

Yet another object of the present invention is utilize viable pollen from a germplasm bank.

Another object of the present invention is a method of producing hybrids from male sterile germplasm such as soybean, wheat, barley, cotton, rye, rice, and sorghum.

BRIEF DESCRIPTION OF THE DRAWINGS

FIG. 6 is a front view of the pollen applicator shown in FIG. 5.

DETAILED DESCRIPTION OF THE PREFERRED EMBODIMENT

Broadly the present invention is a method of field production of hybrid crops with dehydrated pollen. Presently field production of hybrid crops includes the use of two parents placed in close proximity to one another. One parent provides the male portion of the reproductive system, the other parent provides the female portion of the reproductive system. The female portion produces a hybrid seed or fruit or vegetable which is harvested.

The present method of field production of hybrid crops improves on the old method in a number of ways. The present invention does not require the presence of both parents in the field. The male portion, i.e. the pollen, is provided mechanically to the flowering female portion. The present invention also improves the previous method of field production of hybrid crops by decreasing the cost associated with the planting, cultivation, herbicides and insecticides application of the male portion. The mechanical application of pollen is more direct and efficient then nature's reliance on wind or insects to carry the pollen to the flower of the female. Thus, less males are necessary to produce the pollen used by the present method than are required in the previous method of field production of hybrid crops.

Additional advantage of the present invention is the male plant can be kept secure. The two plants necessary to produce a hybrid cross are according to the present invention not located in the same field. Therefore, the germplasm is more secure from theft.

The present invention eliminates one of the most difficult field production issues, making certain that the male is pollinating when the female is flowering. This timing issue is referred to as the nick. The present invention permits the male to be grown in a previous season and its pollen stored or alternatively grown in an earlier region within the same season and its pollen stored until the appropriate time for application to the female. Thus, the planting of the male and female in the same field is no longer an issue.

The present invention has a first requirement. There must be a method of viably storing the pollen required for the hybrid production field. Any method of storing pollen in a viable state can be employed. However, some pollens, notably maize, have heretofore been almost impossible to preserve in a viable state. Since there is wide scale use of field product of hybrids in the maize industry, this is an essential step.

The present method can be used in the maize hybrid production fields because of the invention of a maize pollen preserving method that allows maize pollen to be stored and remain viable.

Figure 1:
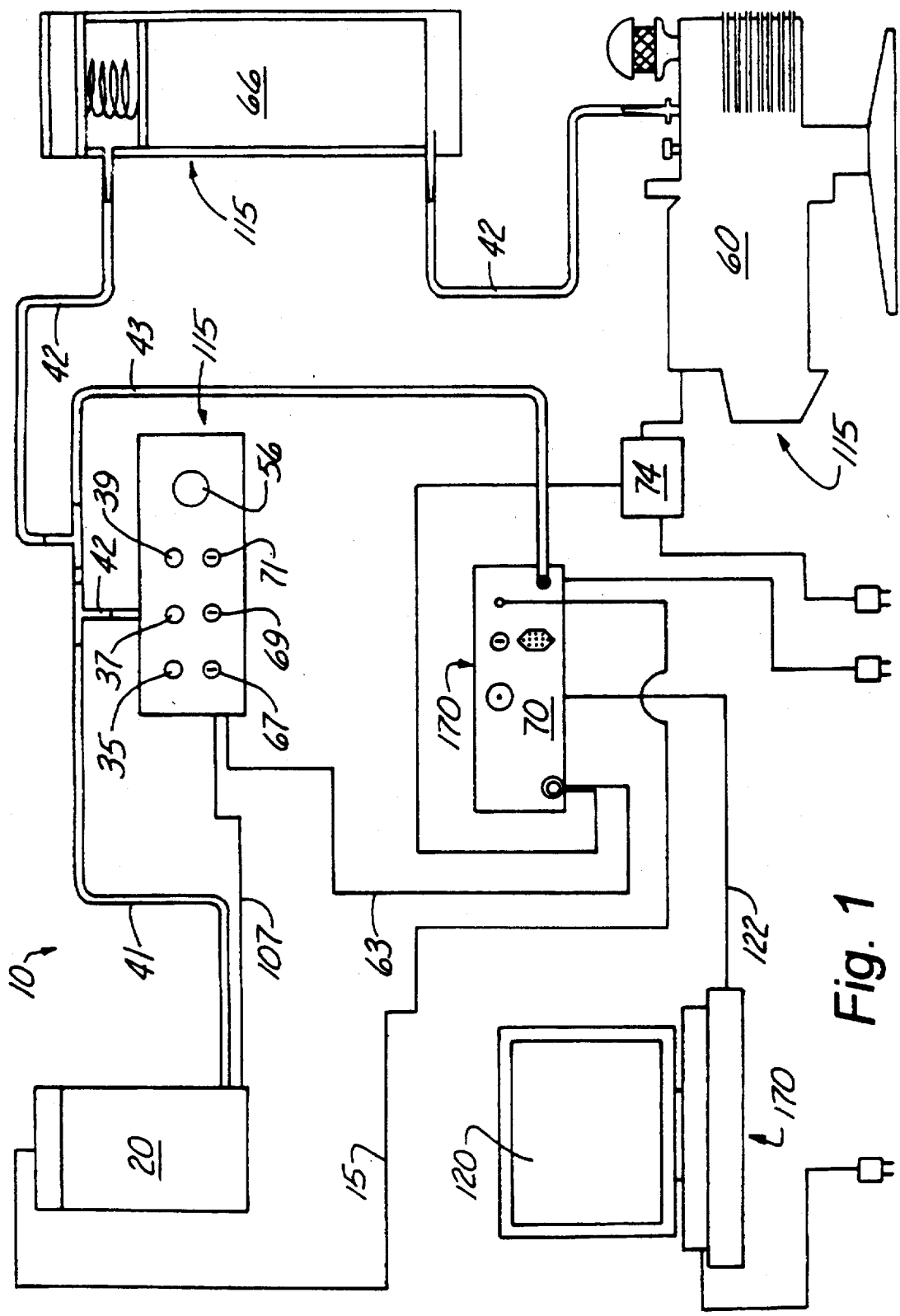
FIG. 1 is a front view of the apparatus according to an exemplary embodiment of a pollen dehydrating machine.
Figure 2:
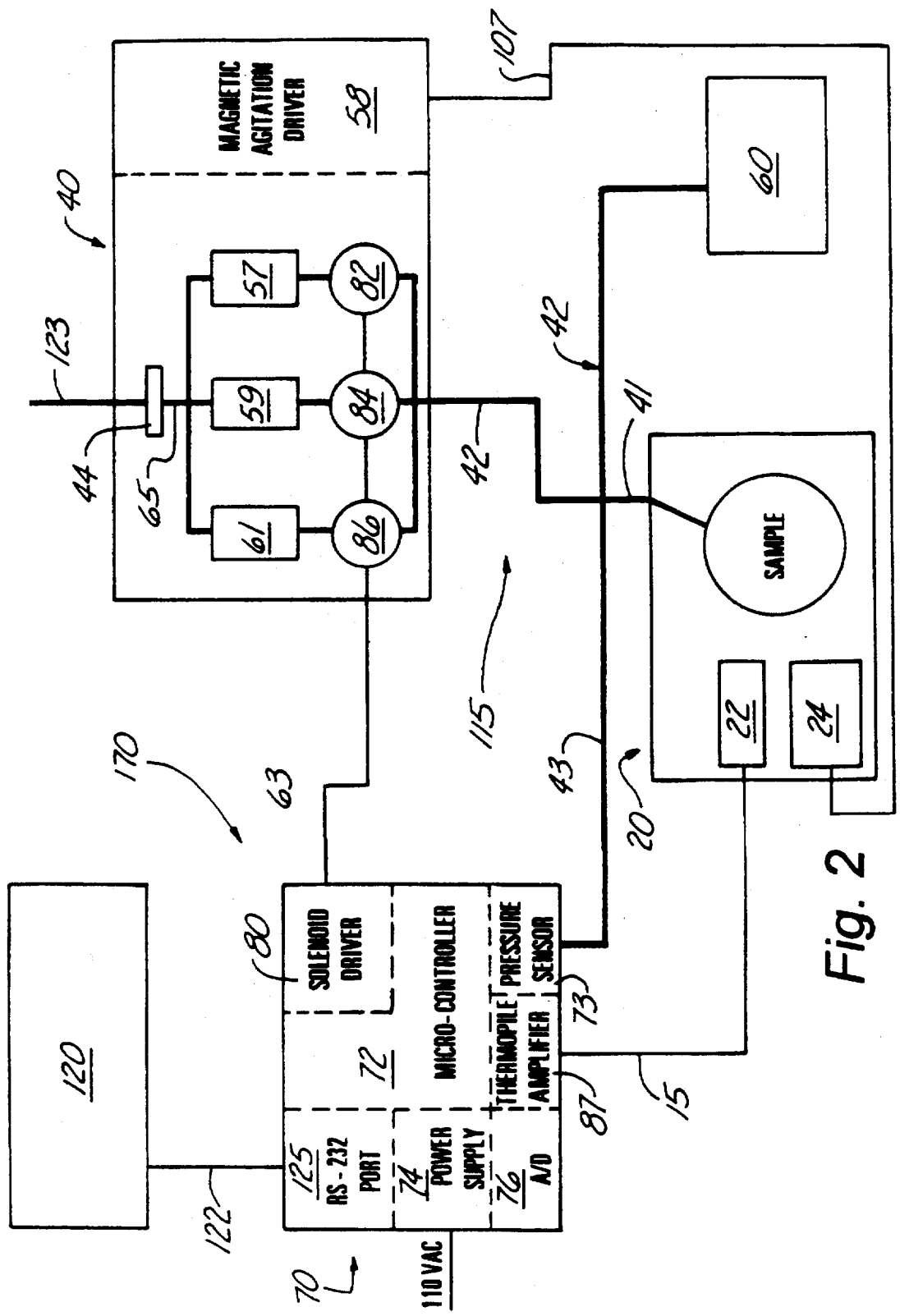
FIG. 2 is a diagram of the apparatus according to an exemplary embodiment in FIG. 1.

The broad aspects of the apparatus of the pollen preparation machine are shown in FIGS. 1 and 2. In FIG. 1 there is shown a diagram of the apparatus 10 which includes a sample chamber 20, a vacuum system 115, and a temperature sensor 22 (see FIG. 2). The vacuum system 115 and the temperature sensor 22 are connected to a computer system 170. The sample chamber 20 is adapted to receive a pollen sample which can be prepared for cryogenic preservation (or other preservation) by removal of pollen moisture by pressure evacuation. The computer system 170 controls the vacuum system 115. The vacuum system 115 is adapted to evacuate sample chamber 20 to reduced atmospheric levels which in turn reduces the pollen moisture. The reduction of pollen moisture is monitored by the temperature sensor 22. The temperature sensor 22 readings are received by the computer system 170 and displayed for the operator when requested. When the pollen reaches the selected level of moisture indicated by the temperature response the cryogenically prepared pollen can be cryogenically stored in a germplasm pollen bank for pollination use at a future time.

The preparation unit has three primary units: the vacuum system, the sample chamber and the computer system. The interaction between the sample chamber 20, the vacuum system 115, and the computer system 170 is best depicted in FIG. 2. Like FIG. 1 the thick bold lines show the vacuum and the thinner lines depict electrical lines. Each of the three primary units includes one of the following three components, the computer interface unit 70, the pressure control box 40, and the sample chamber 20. A standard vacuum pump 60 and standard computer 120 were also used. The computer interface unit 70 houses all the electrical components. The pressure control box 40 houses gas solenoid control valves 82, 84, 86, needle valves 57, 59, 61, and a filter 44 for incoming air. Electrical cables and vacuum lines run between all three elements of the system as well as to the computer 120 (cables only) and vacuum pump 60. Cable shielding was used on the thermopile signal. The sample chamber 20 is grounded directly to the thermopile amplifier circuitry housed within the computer interface unit 70.

The vacuum system 115, includes a vacuum pump 60 which is connected by vacuum line 42 to a desiccator 66 which is connected by vacuum line 42 to a pressure control box 40. The pressure control box 40 (also called the gas control unit) has a port 110 on to which the vacuum line 42 is connected. The vacuum line 42 has two vacuum line segments 41, 43 which are connected through a T joint to the sample chamber 20 and the computer interface unit 70 of the computer system 170, respectively. These vacuum lines 41, 42, 43 connect vacuum system 115 to the computer system 170 and the sample chamber 20. The invention is activated by connection with power source 74. When activated the evacuation of sample chamber 20 by the vacuum system 115 is monitored and controlled by the computer system 170.

Figure 3A:
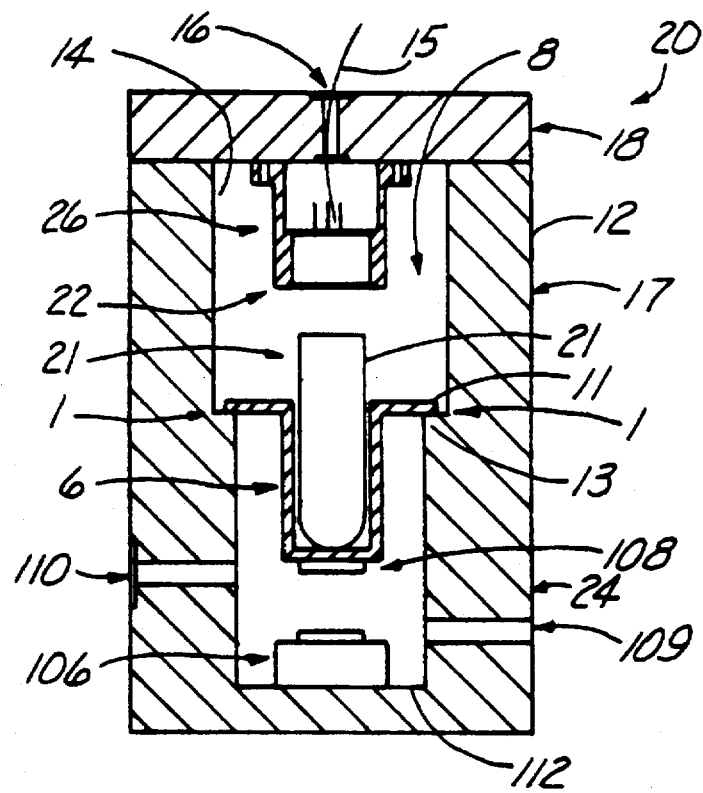
FIGS. 3A–3B are a side view of the cross section of the sample chamber of the apparatus.
Figure 3B:
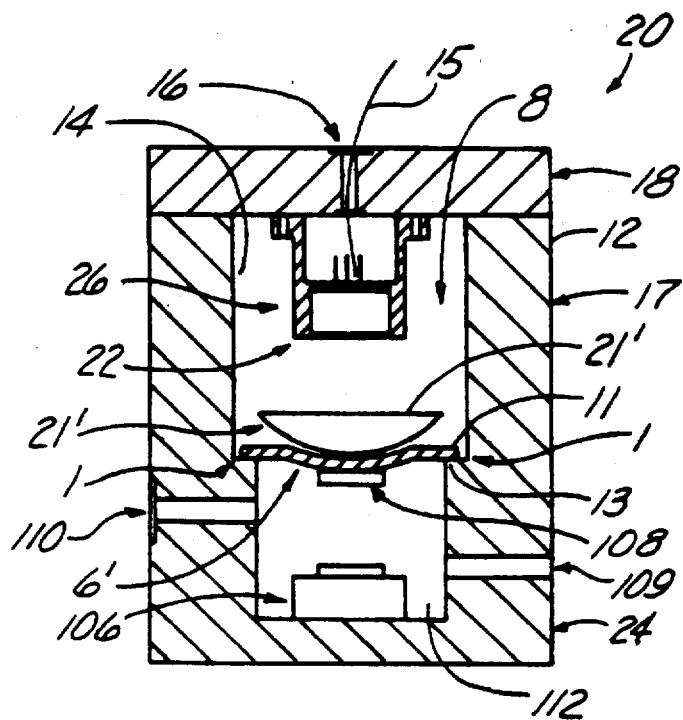

The main component of vacuum system 115 is pressure control box 40 which performs two distinct functions. One function is pressure related. The second function is not pressure related. The first function of the pressure control box 40 is to magnetically agitate the pollen sample within the sample chamber 20 (see FIG. 3). One adjustment valve depicted on the face of the pressure control box 40 is a speed control adjustor 56 for the magnetic agitator drive 56 which powers the magnetic agitator within the sample chamber 20. The agitation by the magnetic agitator avoids uneven release of moisture from the pollen sample when the sample chamber 20 is evacuated. The magnetic agitator may increase the temperature within the sample chamber 20, thus creating unwanted stress on the sample pollen. Another option to having the magnetic agitator within the chamber is to have the magnetic agitator outside of the sample chamber 20. Other alternatives include physical agitation of the entire sample chamber 20, or placing the sample pollen in a single pollen layer on a sample receptor formed as a rectangular platform having a lid. The lid avoids pollen dispersion within the chamber due to evacuation. The present invention has a dish shaped sample receptor 21.

The second function of the pressure control box 40 is to flux or pulse the pressure level in the sample chamber 20. The pressure control box 40 has three light emitting diodes 35, 37, 39 each responsive to a respective solenoid control valves (see FIG. 1). Each of the three gas solenoid control valves 82, 84, 86 have an associated needle valve which can be manually adjusted by a first needle valve adjuster 67, a second needle valve adjuster 69, a third needle valve adjuster 71, respectively. These needle valve adjusters 67, 69, and 71, permit the pressure flux or pulse change in the sample chamber 20 to be adjusted. The pressure can be deceased or increased. Additionally the length of the pressure pulse can be adjusted and the length of time between pulses can be adjusted.

Other methods of preserving pollen can be used. The present invention does not depend on the method of preserving pollen. The present invention is involved in the use of this preserved pollen in the field production of hybrid crops.

The broad steps of the present method are producing the plants having the female portion until the female portion is flowering, accessing a source of viable pollen, applying the pollen to the flowering portion of the female, and harvesting the desired product from the female.

The first step of the present invention involves producing the female portion of the hybrid. This means different things for different crops. For example, in certain hybrid fruits, it may mean nurturing the grown tree. In other crops like sunflower and maize, for example, it may mean planting on an annual or semi-annual basis the female plants.

The female must be cared for so it can achieve the flowering stage. This flowering stage is defined as the time in which the plant is capable of interacting with the pollen to form the hybrid seed, fruit or vegetable. The female can be cytoplasmically male sterile or detasseled or chemically treated, all defined as male sterile.

The step of accessing viable pollen, of course, requires a source of viable male pollen. The apparatus 10 includes pollen collection system (see FIG. 4). This system can be removably mounted to the chassis to permit the chassis to be fitted as the pollen collector or the pollen applicator. The pollen collection system includes a tassel displacement rod 22 which is adjustably positioned to the height of most of the tassels in the field. In a spaced apart relationship with the rod 22, is the pollen suction funnel 24. This funnel 24 is elongated and extends from one side of the chassis to the opposing side. The funnel 24 is adapted to collect the pollen from the displaced tassels of the plants in the field. A vacuum is created in the funnel 24 by the vacuum pump 26. An optional guard can be connected to the chassis and located below the funnel 24 located between crop rows to eliminate any debris from the ground being vacuumed in with the pollen. The vacuum draws the pollen through the feed pipe 28 into a pollen filtering tank housed within the pollen filter housing 30. The number of filters 32 can be decreased or increased, as long as the tassel parts and other debris are removed prior to storage of the pollen. This apparatus allows the purification of the pollen before the pollen travels through the feed pipe 34 into the pollen collection vessel 36. The filters 32 are of an increasingly less coarse grade so that the debris is caught prior to the pollen entry into the feed pipe 34. The pollen is collected in the pollen collection vessel 36. When the vessel is filled, it is transferred to a preservation unit for preparation. The pollen is preferably transfered to a preparation unit within four to six hours of collection to avoid pollen deterioration. Access to viably stored pollen in germplasm banks is sightly limited. Therefore the present invention includes an apparatus for large scale pollen collection. The collected pollen can be stored in a germplasm bank or temporary stored for short terms. Although the use of pollen application to females requires less male plants than would be required in the typical large scale production field, males still have to be grown for the pollen to be collected. In most hybrid production there are inbred plants which act as parent. One is developed it must be increased and tested. When inbred seed is being increased the inbred plants are located in fields which are isolated from other fields so that the inbred pollinates itself.

Figure 4:
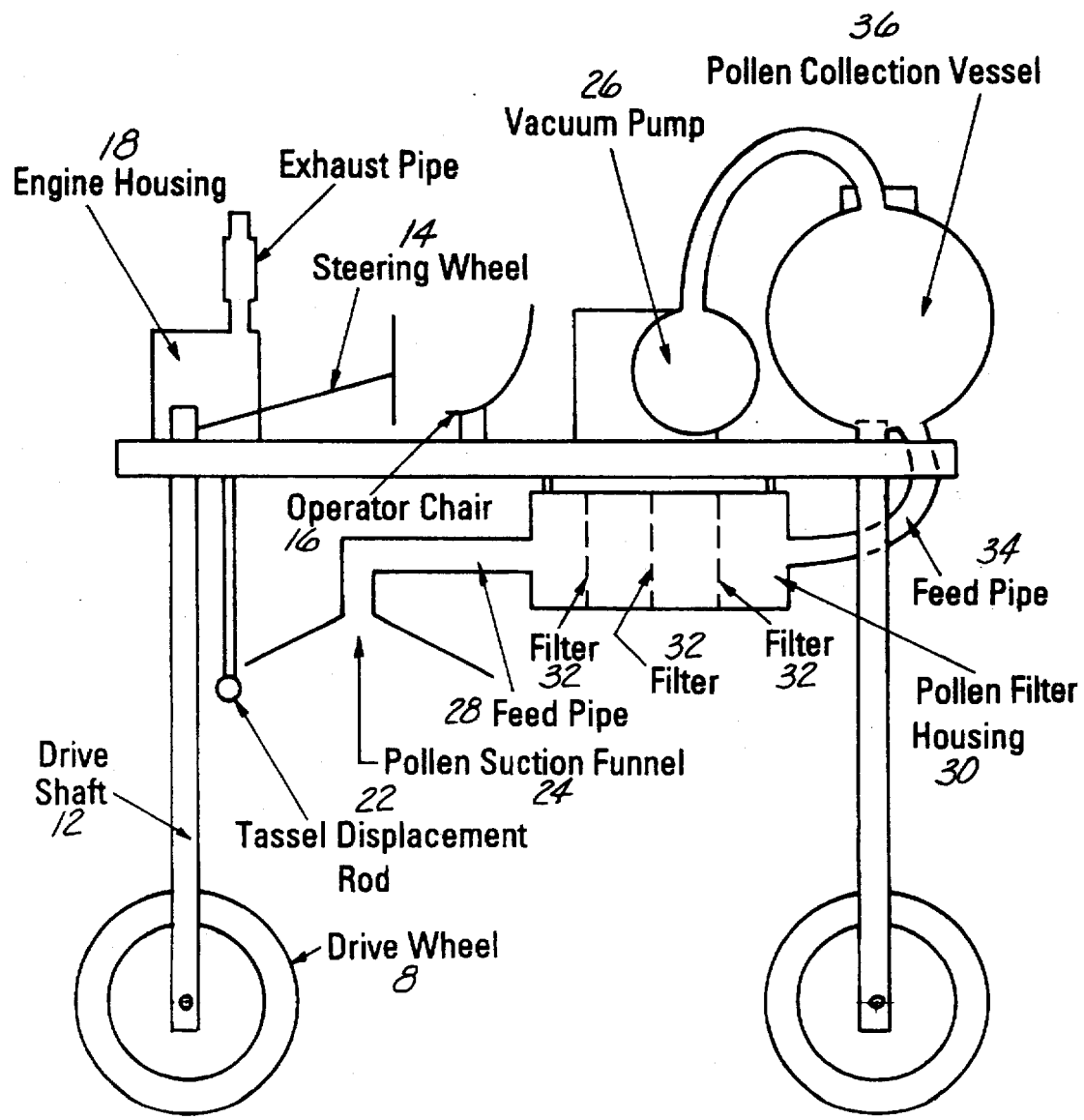
FIG. 4 is a side view of a mechanical pollen collection vehicle which uses a combination of a vacuum, filters, and a temporary pollen collection vessel.

Pollen collection for use in establishing or increasing a germplasm bank or for short term storage prior to use, is collected from male inbreds. Preferably, the male inbreds in an increase field are allowed to shed pollen for a number of days to allow set of seed on the male inbreds. Prior to completion of the pollen shed, the pollen collection vehicle is driven through the field to collect viable pollen. An embodiment of the pollen collection vehicle is shown in cross-section in FIG. 4. An embodiment of the same chassis retrofitted to be a pollen applicator vehicle in FIGS. 5–6. In FIG. 4 the apparatus is configured for pollen collection.

Figure 5:
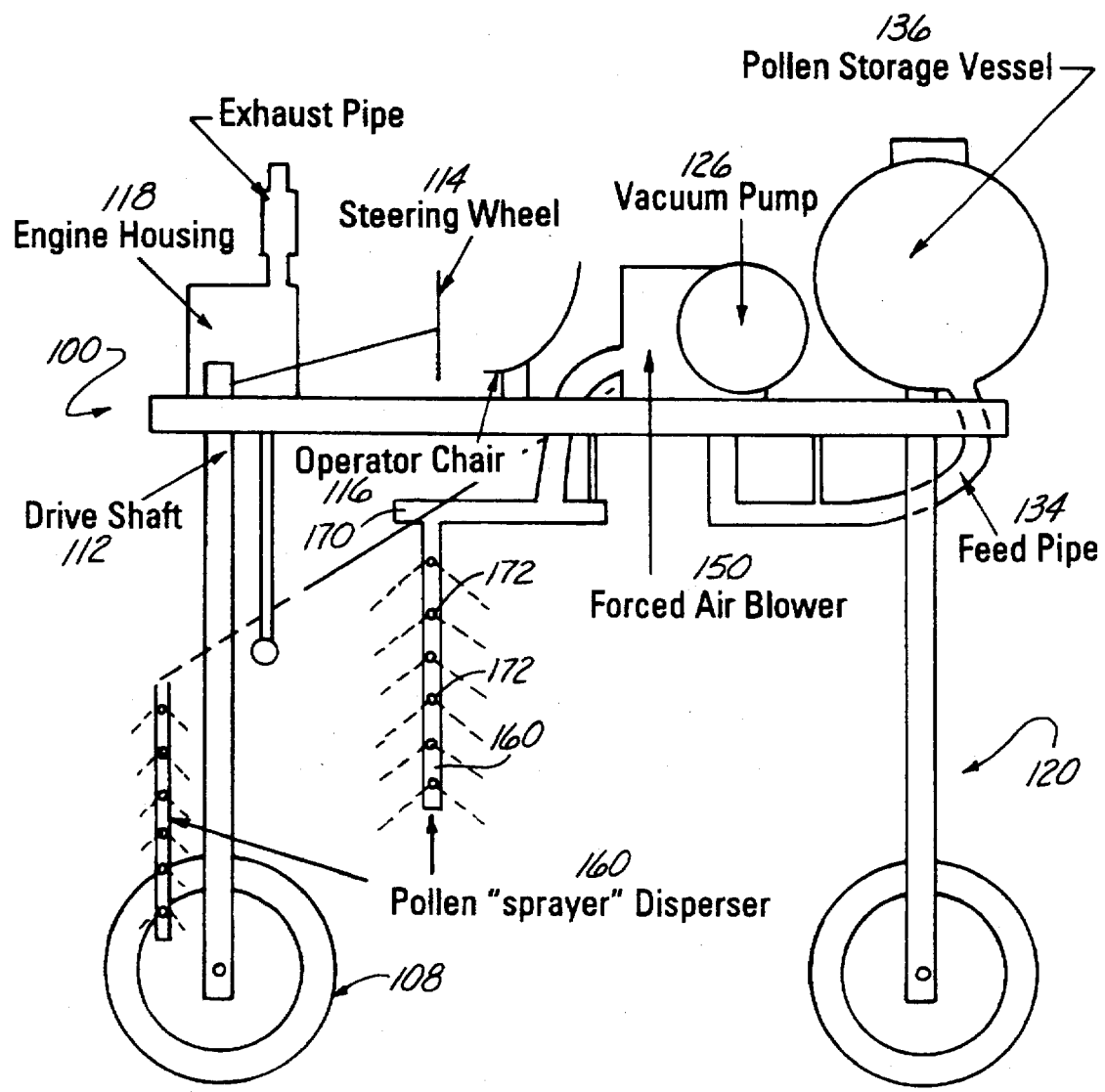
FIG. 5 is a side view of a mechanical pollen applicator vehicle which distributes stored pollen via forced air dispersed at ear height.
Figure 6:
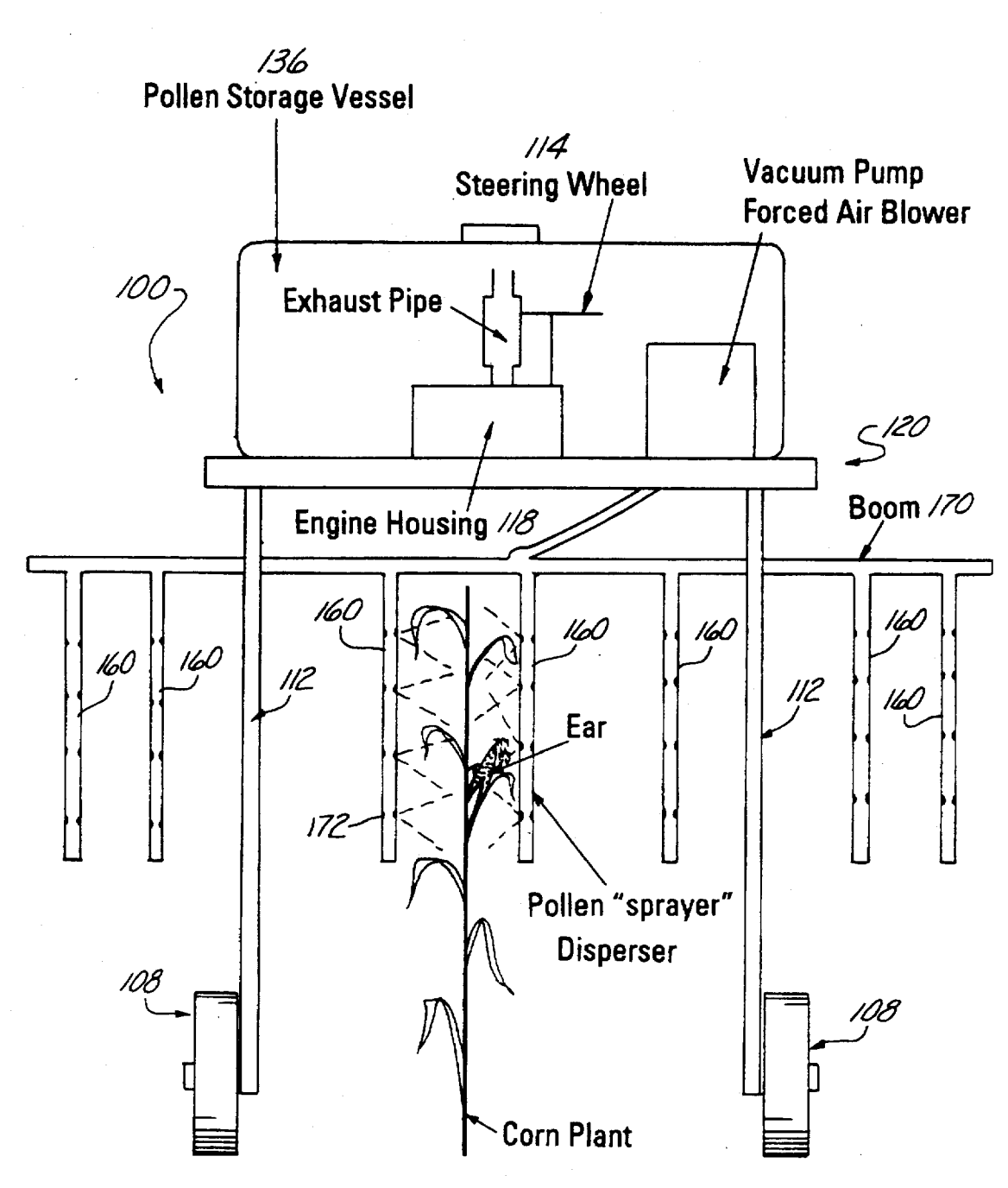

Physically vacuuming up the pollen into the collection vessel. In FIGS. 5–6 the apparatus is configured for pollen dispersion. Physically projecting the collected pollen on to the flowering females. Obviously this device can be adapted to eliminate the drive mechanism such the it can be connected pulled through low height crop fields behind a tractor. Clearly the clearance is not necessary for cotton, barley, oats, wheat, rye, and the like.

Turning to FIG. 4 the embodiment shown clearly has a vehicle chassis 20 with a set of wheels including drive wheels 8 on the front of the vehicle, a drive shaft 12 and a steering mechanism including a steering wheel 14 proximate the operator seat 16. This apparatus 10 includes the fuel reservoir (not shown) and the engine within the engine housing 18 which is adapted to propel the chaises through the crop rows. Clearly, if the crop is of such a stature that a tractor can travel through the field when the pollen is shedding then the chassis does not need to be motorized but can be pulled by the tractor. The apparatus 10 shown in this Figure is especially useful for crops that are tall such as the sorghum and maize.

Depending on the type of pollen, there may be various methods of preserving the pollen. Thus, transportation of the various types of preserved pollen from the germplasm bank to the production field may differ. However, when the present method is used in corn or sunflower fields, the accessed pollen will most likely be stored in liquid nitrogen or freezer units. The essential requirement being that the pollen be at least partially viable so that there is sufficient interaction with the female to have a full production of the desired seed, fruit and/or vegetable.

The step of applying the pollen again varies based on the female and the way the pollen is preserved. The preserved viable pollen is applied generally to the female plant and in some instances directly to the flower. In maize field production of hybrids, it is preferred that the application be rapidly achieved. Maize pollen is stored in a viable state in liquid nitrogen. Thus, once the pollen is requested from the germplasm bank, it must be shipped to the field location. This shipping can be done in liquid nitrogen containers or alternatively the pollen can be transferred to the fields in dry ice or if the distance of travel is not great, in freezer trucks. Once the maize pollen is at the field site, it must remain in storage conditions for as long as possible. It is preferred with maize pollen that it be applied to the flowering plant within four to six hours of its removal from the storage environment. This eliminates unnecessary deterioration of the pollen.

The step of application of the preserved pollen to the female can be implemented in a number of ways depending on the female and the type of storage necessary for the male. Examples of pollen application can be the use of fans, compressors, and the like, to create artificial wind to blow the pollen on the flowers of the female or mechanical application (FIG. 5). Alternatively, if the best method is insect carriers, then insects can be contacted with the pollen and released in the proximity of the female.

In maize and sunflower hybrid production fields, the application can be done mechanically with farm equipment. An example of a pollen applicator useful in maize fields is shown in FIG. 5. The dispersal nozzles of the applicator boom can be adjusted to various heights so that the flowering portion which can be at various heights are all routinely pollinated.

FIGS. 5 and 6 show a front and side view of a pollen application apparatus 100. The application apparatus 100 has a vehicle chassis which can be motorized. Like the collection apparatus 10, the application apparatus includes a vehicle chassis 120 with a set of wheels including driving wheels 108, drive shafts 112 and a steering mechanism including a steering wheel 114 located near the operator chair 116. The application apparatus 100 is propelled by an engine within the engine housing 118.

The application apparatus 100 also includes a pollen dispersal system which includes the pollen storage vessel 136 which is connected by feed pipe 134 to vacuum pump 126. Vacuum pump 126 draws the pollen through the feed pipe 134 and the forced air blower 150 forces the pollen down through the pollen sprayer dispersers 160 which are downwardly projecting from the boom 170. The pollen sprayer dispenser 160 has numerous outlets 172 on the sides of the dispenser 160 to permit the pollen of flowers at various levels.

In operation then the pollen is transported from the storage vessel, through the lines, to the various spray outlets. These spray outlets are adapted to release the pollen under slight pressure such that the pollen is propelled and dispersed toward the tassels of the female maize plant. The lines are connected to a tank containing the pollen. The pollen can be placed in an non-aqueous carrier material to assist in the movement of the pollen from the tank, through the lines and out of the outlets. It is essential that this carrier material does not substantially interfere with the pollination process. When pollinating with maize pollen, it is preferred that the pollen be introduced to the tassel within four to six hours of reaching 72° F.

After the mechanical application of the pollen to the female is completed, the next step is harvesting the desired material from the female. Again, harvesting methods are generally well known to those skilled in the art of field production of hybrid crops. In maize harvesting is of the cob and is done with a combine harvester or a corn picker. Different fruits and vegetables may require manual labor to pick the desired products.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

We claim:

1. A method of producing reproductive crop material formed from at least two parents, the first parent providing the female portion of the reproduction and at least one second parent providing the male pollen portion of the reproduction, comprising the steps of:

a) planting the first parent which contributes the female portion of the crop;

b) providing preserved pollen, which has been preserved by a pulsed pressure evacuation system that reduces pollen moisture content prior to cryogenic storage and providing said preserved pollen mechanically to the female portion of the first parent; and c) harvesting the reproductive crop material from the first parent.

2. A method according to claim one wherein the first parent is a male sterile selected from the group consisting of wheat, oats, barley, rice, rye, sorghum, soybean, maize and cotton.

3. A method according to claim one wherein the reproductive crop material is hybrid.

4. A method according to claim one wherein said first parent is a male sterile plant and said second parent is a plant of similar genetic background which is not male sterile.

5. A method according to claim one wherein the preserved pollen is maize pollen.

6. A method according to claim five wherein the preserved pollen is popcorn pollen.

7. A method according to claim five wherein the preserved pollen is sweet corn pollen.

8. A method according to claim five wherein the preserved pollen is dent corn pollen.

9. A method according to claim one wherein the preserved pollen is dehydrated.

10. A method according to claim nine comprising the step of rehydrating the preserved pollen.

11. A method according to claim one comprising the step of contacting the preserved pollen with a carrier material prior to its mechanical application to the first parent.

12. A method of producing maize crop material formed from at least two parents, the first parent providing the female portion of the reproduction and at least one second parent providing the male pollen portion of the reproduction, comprising the steps of:

a) planting the first parent which contributes the female portion of the crop;

b) providing mechanically preserved pollen, said pollen having been collected in a previous crop season from the second parent and said pollen having been viably preserved by a pulsed pressure evacuation system that reduces pollen moisture content prior to cryogenic storage, to the female portion of the first parent; and c) harvesting the maize crop material from the first parent.

13. A method according to claim 12 wherein the pollen is selected from the group consisting of maize, cotton, sorghum, soybeans, oats, rye and barley.

14. A method according to claim 13 wherein said first parent is a male sterile plant.

15. A method of collecting pollen from a group of pollen producing plants comprising the steps of:

a) planting plants in a group, said plants having a male portion capable of shedding pollen;

b) vacuuming the pollen from the male portion of the plants; and c) preserving the pollen by pressure evacuation monitored by remote indirect sensor and storing said pollen cryogenically so that it is in a viable condition for future use.

16. A method according to claim 15 wherein the pollen is vacuumed by an apparatus having a tassel displacement rod.

17. A method of producing hybrid reproductive crop material according to claim 12 wherein said first parent is a hybrid.

* * * * *